(12) United States Patent
Fan et al.

(10) Patent No.: US 12,220,574 B2
(45) Date of Patent: Feb. 11, 2025

(54) MASK INSTRUMENT AND METHOD FOR USING THE SAME

(71) Applicant: Beijing FUNATE Innovation Technology Co., LTD., Beijing (CN)

(72) Inventors: Li Fan, Beijing (CN); Li Qian, Beijing (CN); Yu-Quan Wang, Beijing (CN)

(73) Assignee: Beijing FUNATE Innovation Technology Co., LTD., Beijing (CN)

(*) Notice: Subject to any disclaimer, the term of this patent is extended or adjusted under 35 U.S.C. 154(b) by 205 days.

(21) Appl. No.: 17/868,935

(22) Filed: Jul. 20, 2022

(65) Prior Publication Data
US 2023/0021540 A1    Jan. 26, 2023

(30) Foreign Application Priority Data

Jul. 21, 2021  (CN) .......................... 202110825751.7
Jul. 21, 2021  (CN) .......................... 202121669111.3

(51) Int. Cl.
*A61N 1/04*    (2006.01)
*A61N 1/32*    (2006.01)
*A45D 44/00*   (2006.01)

(52) U.S. Cl.
CPC .............. *A61N 1/328* (2013.01); *A61N 1/048* (2013.01); *A61N 1/0484* (2013.01); *A45D 44/002* (2013.01)

(58) Field of Classification Search
CPC ...... A61N 1/328; A61N 1/048; A61N 1/0484; A61N 1/36014; A61N 1/0496; A61N 1/3603; A45D 44/002
See application file for complete search history.

(56) References Cited

U.S. PATENT DOCUMENTS

| 11,229,791 B2* | 1/2022 | Fan ..................... A61N 1/0476 |
| 2010/0241056 A1* | 9/2010 | Lehtoluoto ............ A61N 1/328 |
| | | 604/20 |
| 2016/0081580 A1 | 3/2016 | Bergelin et al. |
| 2021/0106822 A1* | 4/2021 | Fan ....................... A61N 1/048 |
| 2021/0213278 A1 | 7/2021 | Fan et al. |

FOREIGN PATENT DOCUMENTS

| JP | 2018183481 | 11/2018 |
| JP | 2020146208 | 9/2020 |
| JP | 2021062192 | 4/2021 |
| TW | M535092 | 1/2017 |
| TW | 202114618 | 4/2021 |
| WO | 2014176420 | 10/2014 |

* cited by examiner

*Primary Examiner* — Ankit D Tejani
*Assistant Examiner* — Joshua Brendon Solomon
(74) *Attorney, Agent, or Firm* — ScienBiziP, P.C.

(57) ABSTRACT

A mask instrument includes a flexible mask and a controller. The flexible mask includes a first flexible layer, a second flexible layer, a plurality of functional layers located between the first flexible layer and the second flexible layer, and a plurality of electrodes electrically connected with the plurality of functional layers. The flexible mask is electrically coupled with the controller via the plurality of electrodes. The second flexible layer comprises at least one hole at a position corresponding to the plurality functional layers, and at least one portion of the plurality of functional layer is exposed out of the second flexible layer from the at least one hole. A method for using the mask instrument is further provided.

19 Claims, 7 Drawing Sheets providing a mask instrument, the mask instrument comprises a flexible mask and a controller, wherein the flexible mask comprises: a first flexible layer; a second flexible layer overlapped with the first flexible layer; a plurality of functional layers sandwiched between the first flexible layer and the second flexible layer; and a plurality of electrodes, two ends of each of the plurality of electrodes are separately electrically connected with a pair of the plurality of functional layers, the flexible mask is electrically coupled with the controller via the plurality of electrodes;

↓ providing a flexible conductive film, applying the flexible conductive film on user's face;

↓ applying the flexible mask on the flexible conductive film; and

↓ applying a voltage to two electrodes of the plurality of electrodes, and forming a least one loop to generate current to stimulate a face skin of a user.

FIG. 5

MASK INSTRUMENT AND METHOD FOR USING THE SAME

CROSS-REFERENCE TO RELATED APPLICATIONS

The application is also related to copending applications entitled, "PHYSIOTHERAPY SHEET AND METHOD FOR USING THE SAME", filed on Jul. 20, 2022, with file Ser. No. 17/868,924.

FIELD

The subject matter herein generally relates to a mask instrument and a method for using the same.

BACKGROUND

As the living standards being improved, demands for beauty are becoming greater. As such, products of beauty flexible masks and beauty instruments are popular, especially the beauty instruments. Beauty instruments which can produce micro-currents to stimulate human faces are favored by consumers. Existing beauty instruments are hand-held beauty instruments and require users to operate the beauty instruments in front of a mirror. This makes the hand-held beauty instruments inconvenient to use.

BRIEF DESCRIPTION OF THE DRAWINGS

Implementations of the present technology will now be described, by way of embodiments, with reference to the attached figures, wherein:

FIG. 5 is a flow chart according to one embodiment showing a method for using a mask instrument.

DETAILED DESCRIPTION

Figure 1:
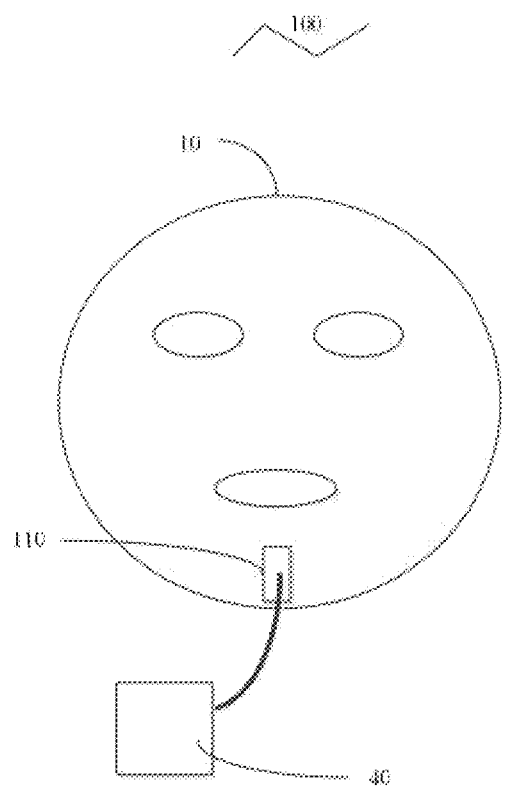
FIG. 1 is a schematic view of a mask instrument according to one embodiment.

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "contact" is defined as a direct and physical contact. The term "substantially" is defined to be that while essentially conforming to the particular dimension, shape, or other feature that is described, the component is not or need not be exactly conforming to the description. The term "comprising," when utilized, means "including, but not necessarily limited to"; it specifically indicates open-ended inclusion or membership in the so-described combination, group, series, and the like.

Figure 2:
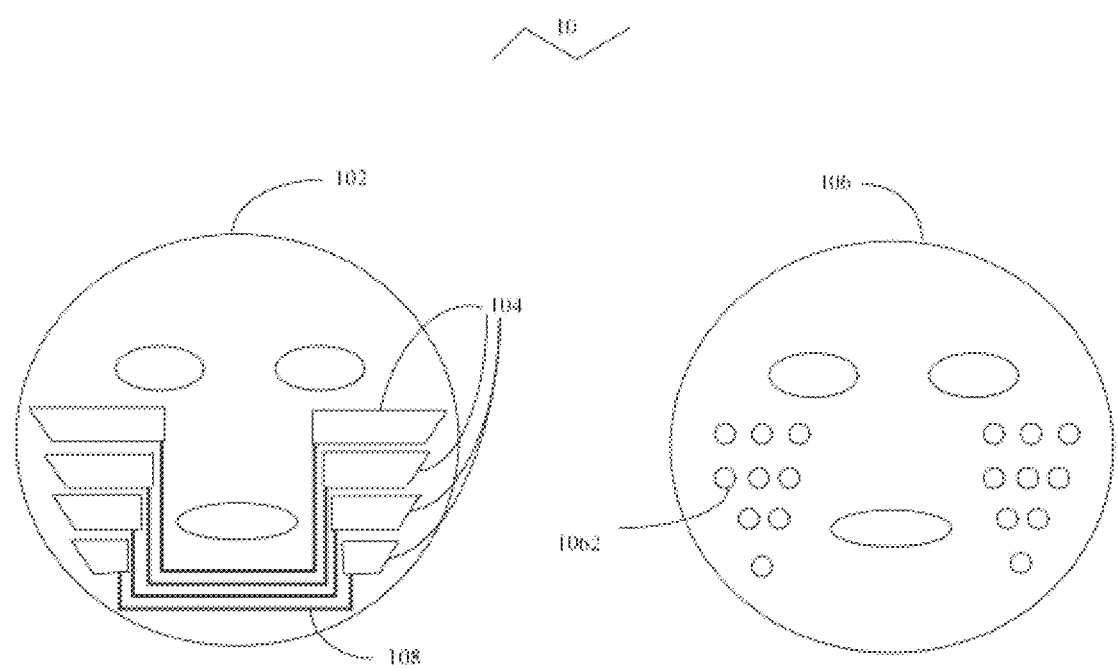
FIG. 2 is a schematic view of a flexible mask in the mask instrument of FIG. 1 according to a first embodiment.

Referring to FIGS. 1 and 2, a mask instrument 10 according to a first embodiment is provided. The mask instrument 10 includes a flexible mask 100 and a controller 200 for controlling the flexible mask 100. The flexible mask 100 includes a first flexible layer 102 and a second flexible layer 106 overlapped with each other (for clarity of display, in FIG. 1, the first flexible layer 102 and the second flexible layer 106 are separately shown), the first flexible layer 102 and the second flexible layer 106 have corresponding eye and mouth openings (not labeled). The flexible mask 100 further includes a plurality of functional layers 104 sandwiched between the first flexible layer 102 and the second flexible layer 106, the plurality of functional layers 104 are symmetrically distributed or regularly distributed, and a plurality of electrodes 108, each of the plurality of electrodes 108 is electrically connected with a single functional layer 104 or a pair of functional layers 104. If a quantity of the plurality of electrodes 108 is defined as K (K=1, 2, 3, 4, 5 . . . ), then a quantity of the plurality of functional layers 104 is 2K (K=1, 2, 3, 4, 5 . . . ) or K. Each electrode 108 is defined as labeled 1, 2, . . . K, and each functional layer 104 or pair of functional layers 104 electrically connected to each electrode 108 is labeled as 1, 2, . . . K. The controller 40 is electrically connected to the K electrodes 108, and controls the plurality of functional layers 104 in the flexible mask 100 through the K electrodes 108. Labeled numbers of the electrodes 108 are irrelevant to the positions of the corresponding functional layers 104, and the corresponding electrode labeled numbers of the adjacent functional layer 104 may not be adjacent to each other. A voltage can be applied to two electrodes in an order 1 and 2, 2 and 3, 3 and 4 . . . K−1 and K, so that the two pairs of functional layers corresponding to each two electrodes are cyclically input current, and the face skin corresponding the two pairs of functional layers are cyclically stimulated. The numbers of the two pairs of functional layers are adjacent, such as numbers 2 and 3, which does not mean that the positions of the two pairs of functional layers are adjacent.

The controller is electrically connected to the K electrodes 108, and the plurality of functional layers 104 in the flexible mask 100 are controlled by the K electrodes 108. In one embodiment, according to FIG. 1, the controller 40 is connected to outside through a connecting wire, the connecting wire includes K wires that are insulated from each other, and each wire is connected to an electrode 108. The controller 40 include a plurality of function buttons for controlling the flexible mask 10. Each function button can control an intensity of current, a frequency of the current, a position where the current is input, etc., so as to control the plurality of functional layers 104 inside the flexible mask and realize different functions. The flexible mask 10 can be movably connected with the controller 40. In this embodiment, the flexible mask 10 is provided with a power inlet 110 on the second flexible layer 106, and the controller 40 is connected to the flexible mask 100 through the power inlet 110.

Figure 3:
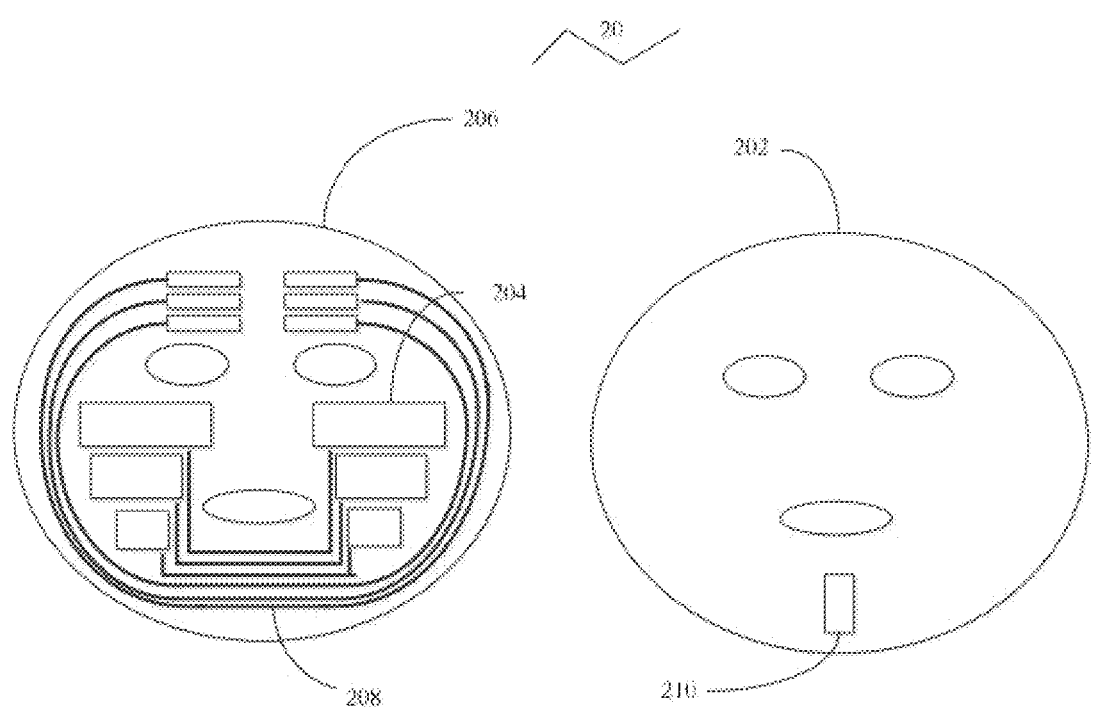
FIG. 3 is a schematic view of a flexible mask in the mask instrument of FIG. 1 according to a second embodiment.

A material of the first flexible layer 102 or the second flexible layer 106 can be a flexible material such as nonwoven fabric, silk, flexible cloth, porous flexible paper, or silica gel, and can be directly attached to a person's face. A thickness of the first flexible layer 102 or the second flexible layer 106 can be set according to actual needs. In this embodiment, the thickness of the first flexible layer 102 or the second flexible layer 106 is in a range from 10 to 100 micrometers. In use of the mask instrument, the second flexible layer 106 will be directly attached on a face. The second flexible layer 106 includes at least one hole 1062 at a position corresponding to the functional layers 104 to expose at least one of the functional layer 104. In FIG. 3, the second flexible layer 106 includes a plurality of holes 1062 spaced with each other at positions corresponding to plurality of functional layers 104. Each of the plurality of holes 1062 makes a portion of each functional layer 104 exposed out of the second flexible layer 106. The function of the plurality of holes 1062 is to expose the functional layer 104. A shape of the at least one hole 1062 is not limited, and can be circular or square. A size of each hole 1062 should be smaller than a size of the functional layer 104 which is corresponding to the hole 1062 to prevent the functional layer 104 from falling off.

As shown in FIG. 2, in a first embodiment, the flexible mask 100 includes 8 functional layers 104. The 8 functional layers 104 are symmetrically distributed at a cheek position of a human face. An area of each functional layer 104 is not limited and can be adjusted as needed. Adjacent functional layers 104 are spaced apart and insulated from each other.

Referring to FIG. 3, in a second embodiment, the flexible mask 100 includes 12 functional layers 204, e.g. 6 pairs of functional layers 204. The 6 functional layers 204 are symmetrically distributed at a cheek position and a forehead position of a human face.

Figure 4:
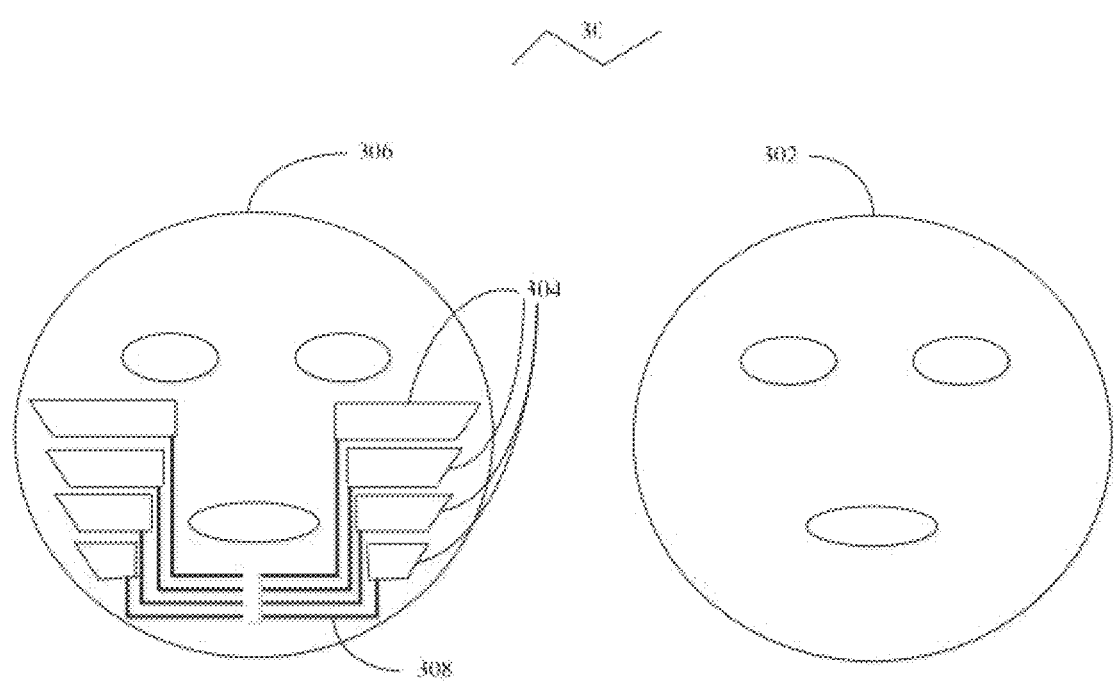
FIG. 4 is a schematic view of a flexible mask in the mask instrument of FIG. 1 according to a third embodiment.

Referring to FIG. 4, in a third embodiment, the flexible mask 100 includes 8 functional layers 304, each electrode 308 is electrically connected with one functional layer 304.

A material of the electrode 108 can be metal, alloy, indium tin oxide (ITO), antimony tin oxide (ATO), conductive silver paste, conductive polymer, or conductive carbon nanotube. The metal or the alloy can be aluminum, copper, tungsten, molybdenum, gold, titanium, rhodium, palladium, iridium, or any alloy thereof. In this embodiment, the K electrodes 108 are all copper wires with a diameter of 1 micrometer. Preferably, an insulating layer can be coated on the surface of each of the K electrodes 108. A material of the insulating layer can be a flexible material.

Each of the plurality of functional layers can be a carbon nanotube layer. The carbon nanotube layer includes a plurality of carbon nanotubes joined by van der Waals attractive force therebetween. The carbon nanotube layer can be a substantially pure structure of carbon nanotubes, with few impurities. The carbon nanotubes in the carbon nanotube layer can be single-walled, double-walled, and/or multi-walled carbon nanotubes. The diameters of the single-walled carbon nanotubes may range from about 0.5 nanometers to about 50 nanometers. The diameters of the double-walled carbon nanotubes may range from about 1 nanometer to about 50 nanometers. The diameters of the multi-walled carbon nanotubes may range from about 1.5 nanometers to about 50 nanometers. The lengths of the carbon nanotubes may range from about 200 micrometers to about 900 micrometers.

The carbon nanotube layer can be a freestanding structure, that is, the carbon nanotube layer can be supported by itself without a substrate. For example, if at least one point of the carbon nanotube layer is held, the entire carbon nanotube layer can be lifted while remaining its structural integrity. Compared with the carbon nanotube layer that is not freestanding, such as the carbon nanotube slurry layer, the freestanding carbon nanotube layer has better flexibility. Experiments have prove that if carbon nanotube slurry is brushed inside the flexible mask 10 as the functional layer 104, after the carbon nanotube slurry is dried, the flexibility of the flexible mask 100 will be reduced due to the carbon nanotube slurry layer.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of the carbon nanotubes arranged along each different direction can be almost the same (e.g. uniformly disordered). The disordered carbon nanotube layer can be isotropic, namely the carbon nanotube layer has properties identical in all directions of the carbon nanotube layer. The carbon nanotubes in the disordered carbon nanotube layer can be entangled with each other.

The carbon nanotube layer including ordered carbon nanotubes is an ordered carbon nanotube layer. The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be selected from single-walled, double-walled, and/or multi-walled carbon nanotubes. The carbon nanotube layer may include at least one carbon nanotube film. In other embodiments, the carbon nanotube layer includes at least one carbon nanotube film or at least one carbon nanotube wire. In other embodiment, the carbon nanotube layer consists one carbon nanotube film or at least two carbon nanotube films. The carbon nanotube layer can include at least two stacked carbon nanotube films.

In some embodiments, the carbon nanotube layer can include a plurality of carbon nanotube wires. In one embodiment, the plurality of carbon nanotube wires can be crossed with each other to form the carbon nanotube layer. In another embodiment, the plurality of carbon nanotube wires can be waved with each other to form the carbon nanotube layer. In other embodiments, the carbon nanotube layer can include only one carbon nanotube wire bended to form the carbon nanotube layer. Each carbon nanotube wire includes a plurality of carbon nanotubes substantially oriented along a same direction (i.e., a direction along the length direction of the untwisted carbon nanotube wire) and joined end to end.

The carbon nanotube layer has a better flexibility than the first flexible layer 102 and/or the second flexible layer 106. When the carbon nanotube layer is used as the functional layer 104 in the flexible mask 10, the flexibility of the entire flexible mask 10 is not decreased by the functional layer 104. The carbon nanotube layer has a large strength, as such, no matter how the flexible mask 100 is bent or pulled, and the carbon nanotube layer is not damaged.

Referring to FIG. 5, the present disclosure further provides a method of using a mask instrument, the method comprises the steps of:

Step S1: Provide a mask instrument, the mask instrument includes a flexible mask, the flexible mask include openings for eyes and mouth, the flexible mask includes: a first flexible layer; a second flexible layer, the first flexible layer and the second flexible layer are stacked with each other, and the first flexible layer and the second flexible layer both include openings for eyes and mouths corresponding to each other; a plurality of functional layers, the plurality of functional layers is located between the first flexible layer and the second flexible layer, each functional layer is a carbon nanotube layer; a plurality of electrodes, each electrode is electrically connected with a pair of functional layers.

The mask instrument can be any one of the mask instruments discussed in the above embodiments.

Step S2: providing a flexible conductive film, applying the flexible conductive film on user's face.

Figure 6:
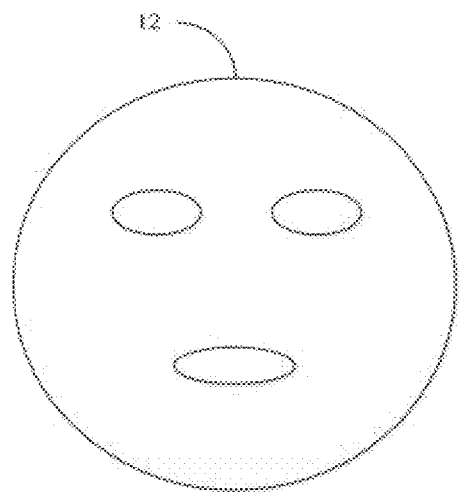
FIG. 6 is a schematic view of a flexible conducting film according to one embodiment.

Referring to FIG. 6, the flexible conductive film 12 is used to directly adhere to the user's face. The flexible conductive film 12 is a conductive material, has certain flexibility, and can fit on the user's face. Preferably, the flexible conductive film has a certain viscosity, and has a certain bonding force with the user's face, so that it can fit the user's face better. In this embodiment, the flexible conductive film 12 is a hydrogel. The hydrogel has a certain viscosity, so that the flexible mask 10 can be completely attached to the surface of the hydrogel flexible conductive film 12, and the hydrogel can be closely attached to the user's skin. Further, the hydrogel has a certain resistance, and its degree of conductivity is moderate. The flexible conductive film 12 can be arbitrarily replaced. In other embodiment, the flexible conductive film 12 can be formed by coating a conductive gel on the user's face.

Step S3: applying the flexible mask on the flexible conductive film.

The flexible conductive film is located between the user's skin and the flexible mask. The second flexible layer of the flexible mask is in contact with the flexible conductive film. Since the second flexible layer includes at least one hole at a position corresponding to the functional layer, the functional layer is exposed out from the second flexible layer, and the functional layer can be directly contacted with the flexible conductive film to electrically connect the functional layer and the flexible conductive film. The flexible conductive film can be used to separate the flexible mask from the user's skin to prevent the flexible mask from being polluted by the skin. Because the flexible conductive film has a low cost, it can be replaced at will. Since the flexible conductive film is a conductive material, it will not affect the flexible mask. Provides electrical stimulation to the user's skin.

Step S4: applying a voltage to two electrodes of the plurality of electrodes, and forming a least one loop to generate current to stimulate the face skin of the user.

In use of the mask instrument, a voltage is applied to two pairs of functional layers or two functional layers via the two electrodes, and a micro-current will be input through the two electrode to the two pairs of functional layers or the two functional layers, and face skin between or under the two pairs of functional layers or the two functional layers will be stimulated by the micro-current. The voltage applied on each two electrodes can be kept for a power-on time, and the voltage is stop for a power-off time, then the voltage is applied to another two electrodes for another power-on time. In some embodiments, the voltage applied on each two electrodes can be in a range of 20V-36V and the frequency of the voltage can be in a range of 50~100 Khz.

When one electrode is electrically connected with a pair of functional layers, a voltage can be applied to a pair of electrodes, and a current can be input to the two pairs of functional layers. When one electrode is electrically connected with to one functional layer, a voltage can be applied to a pair of electrodes to input current on the two functional layers. Specifically, when one electrode is connected to one functional layer, a voltage is applied between any two electrodes to form a circuit loop on the left or right side of the flexible mask. In the circuit loop, the current flows through a power, a first electrode of the plurality of electrodes, the functional layer electrically connected to the first electrode, the flexible conductive film, the user's facial skin, the flexible conductive film, the functional layer electrically connected to the second electrode, and the second electrode. The functional layer electrically connected with the first electrode and the functional layer electrically connected to the second electrode are located on a same side of the flexible mask. When an electrode is connected to a pair of functional layers, when a voltage is applied between any two electrodes, two parallel circuit loops are formed. In each circuit loop, the current flows through the power, the first electrode of the plurality of electrodes, the functional layer electrically connected to the first electrode, the flexible conductive film, the user's facial skin, the flexible conductive film, the functional layer electrically connected to the second electrode, and the second electrode.

The flexible mask is divided into left and right sides according to the position of the user's cheeks. The two functional layers in one loop are located on the same side of the flexible mask.

The voltage can be applied to two electrodes in an order 1 and 2, . . . K-1 and K (K is the numbering of each electrode), so that the two pairs of functional layers corresponding to each two electrodes are cyclically input current, and the face skin corresponding the two pairs of functional layers are cyclically stimulated. The numbers of the two pairs of functional layers are adjacent, such as numbers 2 and 3, which does not mean that the positions of the two pairs of functional layers are adjacent. The positions of the two pairs of functional layers adjacent to each other can be arbitrarily set according to actual needs.

Figure 7:
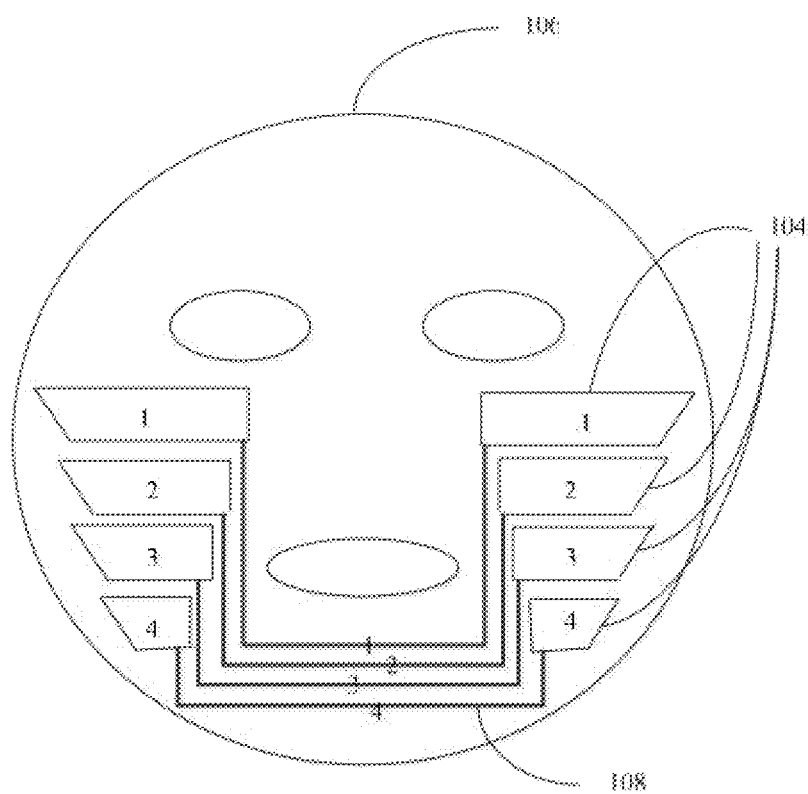
FIG. 7 shows schematic views of functional layers' numberings in a mask instrument according to one embodiment.

Taking the mask instrument provided in the first embodiment as an example, when one electrode is connected to a pair of functional layers, the numbering diagram is as shown in FIG. 7. For clearer description, the two functional layers 104 electrically connected to the same electrode 108 are numbered the same as the electrode 108, and are divided into a left functional layer 104 and a right functional layer 104 according to the position of the functional layer 104. When the flexible mask 10 is electrically connected to an external power and is supplied with an electrical signal, a voltage is applied between any two electrodes 108. For example, when a voltage is applied between two electrodes numbered 1 and 2, two circuit loops are formed simultaneously. In the first circuit loop, the current flows through the external power, the electrode 108 numbered 1, the left functional layer 104 numbered 1, the flexible conductive film, the user's facial skin, the flexible conductive film, and the left function numbered 2, the electrode numbered 2. In the second circuit loop, the current flows through the external power, the electrode 108 numbered 1, the right functional layer 104 numbered 1, the flexible conductive film, the user's facial skin, the flexible conductive film, and the right function numbered 2, the electrode numbered 2. That is, the two functional layers 104 on the left side and the two functional layers 104 on the right side are arranged in parallel. Any two functional layers 104 on the same side are connected in series, and a microcurrent flows through the skin of the user's face between the two functional layers 104 connected in series, so as to locally stimulate the skin. It can be understood that when one electrode 108 is connected to one functional layer 104, a circuit loop is only formed on the left or right side of the flexible mask 10.

From the circuit loops formed above, it can be known that the flexible conductive film 12 should have a certain resistance, so that the current in the circuit loop is transmitted to the user's skin along the thickness direction of the flexible conductive film 12, rather than along the surface parallel to the flexible conductive film 12.

Please refer to FIG. 7, in this embodiment, according to the order of electrode labeled 1 and 2, 2 and 3, 3 and 4 a voltage is applied between two electrodes 108. Two pairs of functional layers 104 are input an electric current to stimulate the skin with electric current circulation. In this embodiment, a power-on time of each pair of electrodes 108 is 0.1 s, and a power-off time is 0.1 s, that is, with a cycle of 0.2 s, first electrify for 0.1 s, then stop for 0.1 s, and so on. Wherein, within 0.1 s of electrification, the voltage between two electrodes 108 can be adjusted in a range between 20-36V, and the frequency is 90 Khz.

The flexible mask can be movably coupled to the controller. The flexible mask defines an access at the window position on the first flexible layer or the second flexible layer, and the controller is connected to the flexible mask through the access. The flexible mask can be changed as needed. The flexible mask can also be cleaned to achieve re-use purpose.

Compared with the prior art, the mask instrument provided by the present invention has the following advantages: first, it can directly fit on a user's face without the need to hold it by hand, which frees the user's hands. Secondly, through controlling a circuit by the controller, the skin on the user's face can be selectively stimulated, and the face parts to be stimulated can be selected more accurately without causing facial asymmetry. Third, the carbon nanotube layer is used as the functional layer, the carbon nanotube layer has a better flexibility than the first flexible layer or/and the second flexible layer, and the flexibility of the entire flexible mask will not be reduced due to the setting of the functional layers, the flexible mask can fit on the user's face well, and the user has a high comfort degree. Fourth, the carbon nanotube layer is used as a functional layer, a strength of the carbon nanotube layer is relatively large, no matter how to bend and pull or clean the flexible mask, the carbon nanotube layer will not be damaged, and the flexible mask has a long life.

The method of using the mask instrument provided by the present invention does not directly attach the flexible facial mask to the user's skin, but uses a flexible conductive film as an intermediate layer, and the flexible conductive film is used to attach the mask instrument to the user's skin. The skin is separated to prevent the mask instrument from being contaminated by the skin, so that the mask instrument can be easily reused. The flexible conductive layer can be replaced at will because of the cost. At the same time, since the flexible conductive film is a conductive material, it will not affect the flexible mask to the user.

Depending on the embodiment, certain blocks/steps of the methods described may be removed, others may be added, and the sequence of blocks may be altered. It is also to be understood that the description and the claims drawn to a method may comprise some indication in reference to certain blocks/steps. However, the indication used is only to be viewed for identification purposes and not as a suggestion as to an order for the blocks/steps.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A mask instrument, comprising:
a flexible mask and a controller configured to control the flexible mask, the flexible mask comprises:
a first flexible layer;
a second flexible layer overlapped with the first flexible layer;
a plurality of functional layers sandwiched between the first flexible layer and the second flexible layer; and
a plurality of electrodes, wherein two ends of each of the plurality of electrodes are separately electrically connected with a pair of the plurality of functional layers, the flexible mask is electrically coupled with the controller via the plurality of electrodes, the second flexible layer comprises at least one hole at a position corresponding to the plurality functional layers, and at least one portion of the plurality of functional layers is exposed out of the second flexible layer from the at least one hole, in a use state of the mask instrument, the flexible mask is attached on a flexible conductive film, the at least one portion of the plurality of functional layers is configured to be directly contacted with the flexible conductive film.

2. The mask instrument of claim 1, wherein the first flexible layer or the second flexible layer defines a window, and the plurality of electrodes are exposed from the window and electrically connected to the controller.

3. The mask instrument of claim 1, wherein a material of the first flexible layer or the second flexible layer is nonwoven fabric, silk, flexible cloth, porous flexible paper, or silica gel.

4. The mask instrument of claim 1, wherein each of the plurality of functional layers is a carbon nanotube layer.

5. The mask instrument of claim 4, wherein the carbon nanotube layer comprises a carbon nanotube film or a plurality of carbon nanotube films overlapped with each other.

6. The mask instrument of claim 4, wherein the carbon nanotube layer is a freestanding structure.

7. The mask instrument of claim 4, wherein the carbon nanotube layer comprises at least one carbon nanotube wire, the at least one carbon nanotube wire comprises a plurality of successive carbon nanotube segments joined end to end by van der Waals attractive force therebetween and oriented along a length direction of the at least one carbon nanotube wire.

8. The mask instrument of claim 7, wherein the carbon nanotube layer comprises one carbon nanotube wire, the carbon nanotube wire is bended to form the carbon nanotube layer.

9. The mask instrument of claim 7, wherein the carbon nanotube layer comprises a plurality of carbon nanotube wires crossed or weaved with each other.

10. The mask instrument of claim 1, wherein the second flexible layer comprises a plurality of holes spaced with each other at positions corresponding to plurality of functional layers.

11. The mask instrument of claim 1, wherein a shape of the at least one hole is circular or square.

12. The mask instrument of claim 1, wherein a size of the at least one hole is smaller than a size of the functional layer.

13. The mask instrument of claim 1, wherein a material of the plurality of at electrodes is metal, alloy, indium tin oxide (ITO), antimony tin oxide (ATO), conductive silver paste, conductive polymer or conductive carbon nanotube.

14. The mask instrument of claim 1, wherein a middle part of each of the plurality of electrodes is electrically connected to the controller.

15. The mask instrument of claim 1, wherein the plurality of functional layers is located at a forehead position, a cheek position, an eye below position, or a nose position.

16. A method for using mask instrument comprising:
providing the mask instrument, the mask instrument comprises a flexible mask and a controller, wherein the flexible mask comprises:
a first flexible layer;
a second flexible layer overlapped with the first flexible layer;
a plurality of functional layers sandwiched between the first flexible layer and the second flexible layer; and
a plurality of electrodes, two ends of each of the plurality of electrodes are separately electrically connected with a pair of the plurality of functional layers, the flexible mask is electrically coupled with the controller via the plurality of electrodes, the second flexible layer comprises at least one hole at a position corresponding to the plurality functional layers, and at least one portion of the plurality of functional layers is exposed out of the second flexible layer from the at least one hole;
providing a flexible conductive film, applying the flexible conductive film on user's face;
applying the flexible mask on the flexible conductive film, the at least one portion of the plurality of functional layers is configured to be directly contacted with the flexible conductive film; and
applying a voltage to two electrodes of the plurality of electrodes, and forming a least one loop to generate current to stimulate the face skin of the user.

17. The method of claim 16, wherein the second flexible layer comprises at least one hole at a position corresponding to the plurality of functional layers.

18. The method of claim 17, wherein the second flexible layer comprises a plurality of holes spaced with each other at positions corresponding to the plurality of functional layers.

19. The method of claim 16, wherein each of the plurality of functional layer is a carbon nanotube layers.

* * * * *